(12) United States Patent
Yuan

(10) Patent No.: US 11,110,194 B2
(45) Date of Patent: Sep. 7, 2021

(54) AROMA CANDLE LAMP WITH 3D SWINGING FLAME

(71) Applicant: Shenzhen Lycas Electronics Co., LTD, Shenzhen (CN)

(72) Inventor: Dan Yuan, Shenzhen (CN)

(73) Assignee: Shenzhen Lycas Electronics Co., LTD, Shenzhen (CN)

(*) Notice: Subject to any disclaimer, the term of this patent is extended or adjusted under 35 U.S.C. 154(b) by 0 days.

(21) Appl. No.: 16/290,986

(22) Filed: Mar. 4, 2019

(65) Prior Publication Data
US 2020/0114038 A1    Apr. 16, 2020

(30) Foreign Application Priority Data

Oct. 16, 2018    (CN) .......................... 201811204455.X

(51) Int. Cl.
*A61L 9/14* (2006.01)
*A61M 21/02* (2006.01)
(Continued)

(52) U.S. Cl.
CPC ............... *A61L 9/14* (2013.01); *A61M 21/02* (2013.01); *F21S 10/046* (2013.01); *F21V 21/26* (2013.01);
(Continued)

(58) Field of Classification Search
None
See application file for complete search history.

(56) References Cited

U.S. PATENT DOCUMENTS

| 9,664,348 B1 | 5/2017 | Chen et al. |
| 10,010,640 B1 | 7/2018 | Li |

(Continued)

FOREIGN PATENT DOCUMENTS

| CN | 201342118 Y | 11/2009 |
| CN | 201394219 Y | 2/2010 |

(Continued)

OTHER PUBLICATIONS

European Search Report issued for the corresponding EP application No. 19 15 2281, dated May 31, 2019, 2 pages (only for informational purpose only).

(Continued)

*Primary Examiner* — Jelitza M Perez
(74) *Attorney, Agent, or Firm* — Viering, Jentschura & Partner MBB

(57) ABSTRACT

An aroma candle lamp with a 3D swinging flame, including a housing and an electronic candle module and an aroma module that are arranged in the housing; the electronic candle module including a simulating flame, a fixture for fixing the simulating flame and a swing device for driving the simulating flame to swing; the aroma module including an aroma component and an aroma fan, wherein the aroma fan is arranged at the top portion of the aroma component, and the aroma fan rotates to drive aroma to spread out from the candle lamp. The candle lamp with a 3D swinging flame and an aroma not only plays a role of lighting and creating an atmosphere, but also has an aroma function for purifying air and making people relaxed. The invention is simple in installation structure, easy to implement, low in cost and convenient in popularization.

12 Claims, 1 Drawing Sheet

(51) Int. Cl.
*F21S 10/04* (2006.01)
*F21V 21/26* (2006.01)
*A61M 21/00* (2006.01)

(52) U.S. Cl.
CPC .............. *A61L 2209/134* (2013.01); *A61M 2021/0016* (2013.01); *A61M 2021/0044* (2013.01)

(56) References Cited

U.S. PATENT DOCUMENTS

| | | | |
|---|---|---|---|
| 2006/0115386 A1* | 6/2006 | Michaels | A01M 1/205 |
| | | | 422/123 |
| 2011/0134628 A1* | 6/2011 | Pestl | F21V 33/004 |
| | | | 362/96 |
| 2014/0177212 A1* | 6/2014 | Li | F21K 9/00 |
| | | | 362/190 |
| 2014/0211499 A1 | 7/2014 | Fong et al. | |
| 2016/0109081 A1* | 4/2016 | Thompson | F21S 10/046 |
| | | | 362/96 |
| 2017/0067608 A1* | 3/2017 | Patton | A61L 9/122 |
| 2017/0122512 A1* | 5/2017 | Yuan | F21S 6/001 |

FOREIGN PATENT DOCUMENTS

| | | |
|---|---|---|
| CN | 103574487 A | 2/2014 |
| CN | 103697410 A | 4/2014 |
| CN | 203628510 U | 6/2014 |
| CN | 203823653 U | 9/2014 |
| CN | 206072948 U | 4/2017 |
| CN | 206989087 U | 2/2018 |
| CN | 207162404 U | 3/2018 |
| CN | 108105711 A | 6/2018 |
| CN | 108167761 A | 6/2018 |
| WO | 2005074998 A1 | 8/2005 |
| WO | 2015080664 A1 | 6/2015 |
| WO | 2018072694 A1 | 4/2018 |

OTHER PUBLICATIONS

Chinese Search Report based on application No. 201811204455X (2 pages) dated Aug. 27, 2020 (Reference Purpose Only).
Supplementary search issued for the corresponding Chinese patent application No. 201811204455, dated Mar. 26, 2021, 2 pages (for informational purposes only).

* cited by examiner

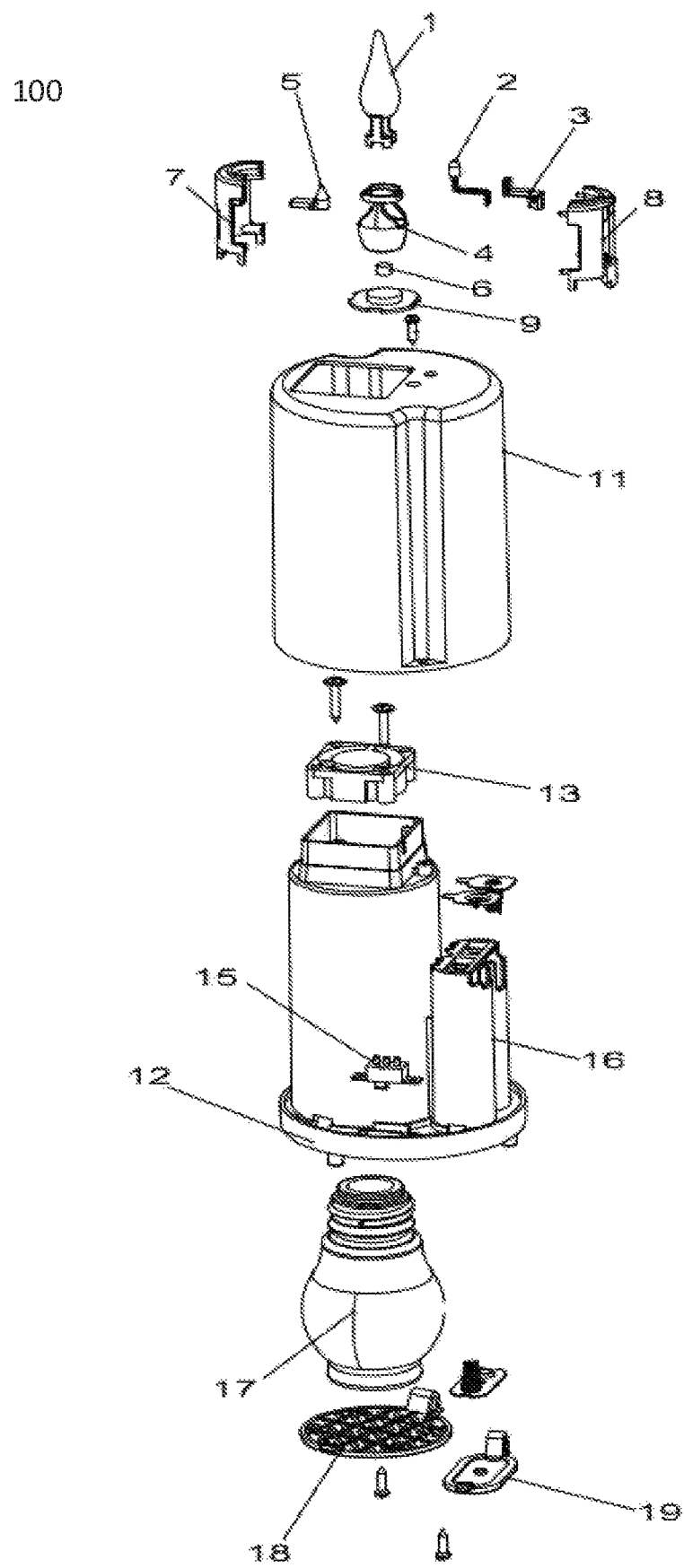

AROMA CANDLE LAMP WITH 3D SWINGING FLAME

CROSS-REFERENCE TO RELATED APPLICATIONS

This application claims priority to Chinese patent application number 201811204455.X filed on Oct. 16, 2018, which is incorporated herein by reference in its entirety.

TECHNICAL FIELD

Various aspects of this disclosure relate to the technical field of electronic candle devices, specifically to an aroma candle lamp with a 3D swinging flame.

BACKGROUND

Candles are not only mainly used for lighting, but also used for decoration. Flicking candle light creates a happy atmosphere for birthday parties, friends' dinners, and dating of people in love. Traditional candles are conveniently operated and have potential safety hazards. Electronic candles solve those problems. However, the candle light of the existing electronic candles looks stiff and not real, and the electronic candles only have a single function and fail to meet more demands of people.

Aromatherapy care is capable of bringing a comfortable feeling, nourishing skin, making people feel relaxed, and releasing pressure. Fragrant oil (also called plant essential oils) can be quickly absorbed in blood and lymph of human by means of massaging, absorption, hot compressing, soaking and fumigation to accelerate metabolism in human body, urge living cells to reproduce, and strength the body's immunity to further adjust the nervous system, circulatory system, endocrine system, mussel tissues, digestion system, excretory system, etc. of human body. The pure plant fragrant oils contain a lot of phytoncide which can stimulate the autonomic nerve of human body and stabilize the endocrine system, so people feel fresh and vigorous. Therefore, aromatherapy is increasing in popularity.

SUMMARY

For this reason, it is necessary to provide an aroma candle with a 3D swinging flame, which is safe and convenient in use, has a high-fidelity flame and an aromatherapy function.

An aroma candle lamp with a 3D swinging flame includes a housing and an electronic candle module and an aroma module that are arranged in the housing; the electronic candle module includes an simulating flame, a fixture for fixing the simulating flame and a swing device for driving the simulating flame to swing; the aroma module includes an aroma component and an aroma fan; wherein the aroma fan is arranged at the top portion of the aroma component; and the aroma fan rotates to drive aroma to spread out from the candle lamp.

Further; the housing may include a housing body and a base; the base and the housing body surround a hollow cavity; the electronic candle module and the aroma module are arranged in the hollow cavity; and the electronic candle module is arranged above the aroma module.

Further, the simulating flame may include a flame body and a light source that is arranged in the flame body; the fixture includes a left cover and a right cover; the right cover has an inside wall fixedly provided with a light source fixing bracket; and the light source is fixedly installed on the light source fixing bracket.

Further; the left cover and the right cover surround a candle lamp cavity; the swing device is arranged in the candle lamp cavity; the swing device includes a support block and a wing bracket, wherein the support block has a support portion and a fixing portion connected to one side of the support portion, the support block is fixedly arranged on an inside wall of the left cover through the fixing portion; wherein the swing bracket includes a top portion that protrudes upward and a magnet holder that is arranged below the top portion, the support portion of the support block is arranged on the inner side of the top portion, the top end of the support portion and the top portion form a contact point, and the swing bracket pivotally swings around the contact point on the top end of the support portion.

Further, the swing device may include a magnet and a control circuit board; the magnet is arranged at the bottom of the magnet holder; the control circuit board is provided with an induction coil; the induction coil is arranged on one side of the magnet; the control circuit board generates a pulse width modulation signal; the induction coil generates a variable magnetic field under the control of the pulse width modulation signal; the magnetic field direction of the induction coil and the magnetic field direction of the magnet are opposite; and the magnet moves by the effect of the magnetic field of the induction coil to drive the swing bracket to swing.

Further, the flame body is installed at the top end of the swing bracket; the flame body covers the light source; the flame body and the fixture keep a clearance there-between; and the flame body moves as the swing bracket swings.

Further, the aroma module may include an aroma component housing and an aroma bottom cover; the aroma component housing and the aroma bottom cover surround an aroma component cavity; the aroma component is arranged in the aroma component cavity; an aroma through-hole is formed on the top portion of the aroma component cavity, and the aroma fan is installed in the aroma through-role.

Further, the aroma component may include an aroma oil bottle and a cotton core and the cotton core extends to the mouth of the bottle from the bottom of the aroma oil bottle for adsorbing the aroma oil in the aroma oil bottle.

Further, an atomizer plate is arranged at the mouth of the aroma oil bottle, and the atomizer plate is used to atomize the aroma oil.

Further, the aroma bottom cover has a plurality of through-holes; the aroma fan rotates such that air flows in via the through-holes, passes through the aroma component cavity, and flows out via the clearance between the flame body and the fixture, so that aroma spreads out from the aroma candle lamp.

In the aroma candle lamp with a 3D swinging flame, the simulating flame swings when driven by the swing device such that the electronic candle lamp generates a vivid high-fidelity flame; and the aroma module drives the aroma oil to spread in the air, achieving an aromatic effect. The candle lamp with a 3D swinging flame and an aroma not only plays a role of lighting and creating an atmosphere, but also has an aroma function for purifying air and making people relaxed. The matter disclosed herein is simple in structure, easy to implement, low in cost and convenient in popularization.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various aspects are described with reference to the following drawings, in which:

FIG. 1 is an exploded structure view of an aroma candle lamp with a 3D swinging flame in an aspect of the disclosure.

DESCRIPTION

In some aspects, the aroma candle lamp with a 3D swinging flame is taken as an example. The disclosure is described in detail below in conjunction with some aspects and attached drawings.

Referring to FIG. 1, an aspect of the disclosure provides an aroma candle lamp 100 with a 3D swinging flame, including a housing 11 and an electronic candle module and an aroma module that are arranged in the housing 11; the electronic candle module includes a simulating flame, a fixture for fixing the simulating flame and a swing device for driving the simulating flame to swing; wherein the aroma module includes an aroma component and an aroma fan 13; the aroma fan 13 is arranged at the top portion of the aroma component, and the aroma fan 13 rotates to drive aroma to spread out from the candle lamp.

Further, the housing 11 also includes a housing body and a base 12; the base 12 and the housing body 11 surround a hollow cavity; the electronic candle module and the aroma module are arranged in the hollow cavity; and the electronic candle module is arranged above the aroma module.

In some aspects, the housing 11 has a flame through-hole on the top portion, and the simulating flame penetrates through the flame through-hole and keeps a distance from the edge of the flame through-hole. In some aspects; the housing 11 has decorative figures or patterns.

Further; the simulating flame includes a flame body 1 and a light source 2 that is arranged in the flame body 1; the fixture includes a left cover 7 and a right cover 8; the right cover 8 is fixedly provided with a light source fixing bracket 3 at the inside wall; and the light source 2 is fixedly installed on the light source fixing bracket 3. The left cover 7 and the right cover 8 surround a candle lamp cavity; the swing device is arranged in the candle lamp cavity; the swing device includes a support block 5 and a swing bracket 4; wherein the support block 5 has a support portion and a fixing portion connected to one side of the support portion, the support block 5 is fixedly arranged on the inside wall of the left cover 7 through the fixing portion; wherein the swing bracket 4 includes a top portion that protrudes upward and a magnet holder that is arranged below the top portion, the support portion of the support block 5 is arranged on the inner side of the top portion, the top end of the support portion and the top portion form a contact point, and the swing bracket 4 pivotally swings around the contact point on the top end of the support portion.

Further, the swing device also includes a magnet 6 and a control circuit board 9; the magnet 6 is arranged at the bottom of the magnet holder; the control circuit board 9 is provided with an induction coil; the induction coil is arranged on one side of the magnet 6; the control circuit board 9 generates a pulse width modulation signal; the induction coil generates a variable magnetic field under the control of the pulse width modulation signal; the magnetic field direction of the induction coil and the magnetic field direction of the magnet 6 are opposite; and the magnet 6 moves by the effect of the magnetic field of the induction coil to drive the swing bracket 4 to swing. The flame body 1 is installed at the top end of the swing bracket 4; the flame body 1 covers the light source 2; the flame body 1 and the fixture keep a clearance there-between; and the flame body 1 moves as the swing bracket 4 swings.

In some aspects, the swing bracket 4 is a shaped as a hollow cylinder; the cylinder has a through-hole on the lateral face; wherein the support block 5 penetrates through the through-hole, the fixing portion of the support block 5 is fixedly installed on the inside wall of the left cover 7, the support portion of the support block 5 is shaped as a cone or spheroid that protrudes upward; wherein the top portion of the swing bracket 4 is shaped as an upward arced projection, the radian of the upward projection of the top portion of the swing bracket 4 is greater than the radian of the support portion, the support portion is supported at the inner wall of the top portion and forms a contact point with the top portion of the swing bracket 4. The bottom of the swing bracket 4 is the magnet holder; the control circuit board 9 is arranged below the swing bracket 4; and the magnet 6 faces the induction coil.

In some aspects, the swing bracket 4 has the bottom with a weight or a weight block such that the swing bracket 4 stands upright in the static state.

In some aspects, the pulse width modulation signal generated by a control circuit on the control circuit board 9 drives the induction coil to generate the variable magnetic field, and the variable magnetic field applies an action force onto the magnet 6 to drive the magnet 6 to move. By the effect of the gravity and inertia of the magnet 6 and the swing bracket 4, the swing bracket 4 irregularly swings by taking the contact point between its top portion and the support portion of the bracket as the circle of center such that the flame body 1 installed on the swing bracket 4 irregularly swings as well.

In some aspects, the control circuit is electrically connected with the light source 2; the light source 2 emits light and projects light onto the flame body 1; the flame body 1 irregularly swings such that the light projected on the flame body 1 presents an unstable state, achieving the effect that the candle light swings along with wind.

Further; the aroma module also includes an aroma component housing and an aroma bottom cover 18; the aroma component housing and the aroma bottom cover 18 surround an aroma component cavity; the aroma component is arranged in the aroma component cavity; an aroma through-hole is formed on the top portion of the aroma component cavity, and the aroma fan 13 is installed in the aroma through-hole. The aroma component includes an aroma oil bottle 17 and a cotton core; the cotton core extends to the mouth of the bottle from the bottom of the aroma oil bottle 17 for adsorbing the aroma oil in the aroma oil bottle 17. The aroma bottom cover 18 has a plurality of through-holes; the aroma fan 13 rotates such that air flows in via the through-holes, passes through the aroma component cavity, and flows out via the clearance between the flame body 1 and the fixture, so that aroma spreads out from the aroma candle lamp.

In some aspects, the base 12 has a base through-hole, and the aroma bottom cover 18 is fastened in the base through-hole.

In some aspects, the aroma oil bottle 17 can be installed and dismantled by opening the aroma bottom cover 18. The aroma oil is filled in the aroma oil bottle 17, and the cotton core is placed in the aroma oil bottle 17. The cotton core adsorbs the aroma oil and enables the aroma oil to volatilize. The aroma fan 13 rotates such that the air flows in via the through-holes of the aroma bottom cover 18, passes through the cavity in the aroma housing, and flows out via the clearance between the housing 11 and the flame body 1. The volatile aroma oil flows along with the air and spreads in air.

In some aspects, the aroma fan 13 is a mute fan.

In another aspect, an atomizer plate is arranged at the mouth of the aroma oil bottle 17; the atomizer plate is used to atomize the aroma oil; and the atomized aroma oil is driven by the aroma fan 13 to spread out.

Further, the aroma candle lamp also includes batteries and a switch 15; the base 12 has a battery seat 19; the housing 11 is internally provided with a battery compartment 16; the battery compartment 16 is arranged on one side of the aroma component housing; and the batteries in the battery compartment 16 can be placed by opening the battery seat 19. The battery compartment 16 is electrically connected to the aroma fan 13 and the control circuit board 9 through the switch 15.

Further, the switch 15 is a toggle switch 15, a touch key switch 15 or an infrared remote control switch 15.

Further, the base 12 has a projecting anti-slip pad; the anti-slip pad prevents the aroma candle lamp 100 from slipping and also ensures smooth flow of air.

For the aroma candle lamp with a 3D swinging flame 100, in the electronic candle module, the simulating flame irregularly swings when driven by the swing device such that the electronic candle lamp 100 generates a vivid high-fidelity flickering effect; and the aroma module drives the aroma oil to spread in the air, achieving an aromatic effect. The fragrance candle lamp with a 3D swinging flame 100 not only plays a role of lighting and creating an atmosphere, but also has an aromatic function for purifying air and making people relaxed, and is also smoke-less, flame-less, safety and environmentally-friendly. The disclosure herein provides devices that are simple in structure, easy to implement, low in cost and convenient in popularization.

While the disclosure has been particularly shown and described with reference to specific aspects, it should be understood by those skilled in the art that various changes in form and detail may be made therein without departing from the spirit and scope of the disclosure as defined by the appended claims. The scope of the disclosure is thus indicated by the appended claims and all changes which come within the meaning and range of equivalency of the claims are therefore intended to be embraced.

What is claimed is:

1. An aroma candle lamp with a 3D swinging flame, comprising:
   a housing comprising a housing body and a base, the housing body and the base surrounding a hollow cavity, wherein an electronic module and an aroma module are arranged in the hollow cavity, and the electronic candle module is arranged above the aroma module;
   the electronic candle module comprising a simulating flame comprising a flame body and a light source that is arranged in the flame body, a fixture for fixing the simulating flame, and a swing device for driving the simulating flame to swing, wherein the fixture comprises a left cover and a right cover, the right cover comprising an inside wall with a light source fixing bracket fixed to the inside wall and with the light source installed on the light source fixing bracket, wherein the swing device comprises a swing bracket and a support block with a support portion and a fixing portion connected to one side of the support portion, wherein the fixing portion is directly fixed on an inside wall of the left cover, wherein the swing bracket rests on the support portion; and
   the aroma module comprising an aroma component housing and an aroma bottom cover surrounding an aroma component cavity; an aroma component arranged in the aroma component cavity; an aroma through-hole formed in the aroma component housing above the aroma component cavity; and an aroma fan, wherein the aroma fan is arranged in the aroma through-hole and the aroma fan is configured to rotate to drive aroma to spread out from the aroma candle lamp.

2. The aroma candle lamp with the 3D swinging flame of claim 1, wherein the left cover and the right cover surround a candle lamp cavity; the swing device is arranged in the candle lamp cavity; wherein the swing bracket comprises a top portion that protrudes upward and a magnet holder that is arranged below the top portion, the support portion of the support block is arranged on an inner side of the top portion, a top end of the support portion and the top portion form a contact point, and the swing bracket pivotally swings around the contact point on the top end of the support portion.

3. The aroma candle lamp with the 3D swinging flame of claim 2, wherein the swing device also comprises a magnet and a control circuit board; the magnet is arranged at a bottom of the magnet holder; the control circuit board comprises an induction coil; the induction coil arranged on one side of the magnet; the control circuit board configured to generate a pulse width modulation signal; the induction coil configured to generate a variable magnetic field under the control of the pulse width modulation signal; wherein a magnetic field direction of the induction coil and a magnetic field direction of the magnet are opposite; and the magnet moves by the effect of the magnetic field of the induction coil to drive the swing bracket to swing.

4. The aroma candle lamp with the 3D swinging flame of claim 2, wherein the flame body is installed at the top portion of the swing bracket; the flame body covers the light source; the flame body and the fixture keep a clearance therebetween; and the flame body moves as the swing bracket swings.

5. The aroma candle lamp with the 3D swinging flame of claim 1, wherein the aroma bottom cover has a plurality of through-holes and is arranged in the base; the aroma fan rotates such that air flows in via the plurality of through-holes, passes through the aroma component cavity, and flows out via a clearance between the flame body and the fixture, so that aroma spreads out from the aroma candle lamp.

6. The aroma candle lamp with the 3D swinging flame of claim 1, wherein the aroma component comprises an aroma oil bottle and a cotton core and the cotton core extends to the mouth of the bottle from the bottom of the aroma oil bottle for adsorbing the aroma oil in the aroma oil bottle.

7. The aroma candle lamp with the 3D swinging flame of claim 6, wherein an atomizer plate is arranged at the mouth of the aroma oil bottle, and the atomizer plate is used to atomize the aroma oil.

8. An aroma candle lamp comprising a housing body and a base surrounding a hollow cavity with an electronic candle module and an aroma module arranged in the hollow cavity, the aroma module arranged below the electronic candle module, wherein
   the electronic candle module comprises a simulating flame comprising a flame body and a light source that is arranged in the flame body, a fixture for fixing the simulating flame, and a swing device for driving the simulating flame to swing, wherein the fixture comprises a left cover and a right cover, the right cover comprising an inside wall with a light source fixing bracket fixed to the inside wall and with the light source installed on the light source fixing bracket, wherein the swing device comprises a swing bracket and a support block with a support portion and a fixing portion connected to one side of the support portion, wherein the fixing portion is directly fixed on an inside wall of the left cover, wherein the swing bracket rests on the support portion, wherein the swing device comprises a magnet and a control circuit board with an induction coil arranged to a side of the magnet, wherein the swing device is configured to drive the swing bracket to swing and cause the simulating flame to move; and the aroma module comprises an aroma component housing and an aroma bottom cover surrounding an aroma component cavity; an aroma component arranged in the aroma component cavity; an aroma through-hole formed in the aroma component housing above the aroma component cavity; and an aroma fan, wherein the aroma fan is arranged above the aroma component cavity in the aroma through-hole and the aroma fan is configured to rotate to drive aroma to spread out from the aroma candle lamp.

9. The aroma candle lamp of claim 8, wherein the left cover and the right cover surround a candle lamp cavity, wherein the swing device is arranged in the candle lamp cavity, wherein the swing bracket comprises a top portion that protrudes upward and a magnet holder that is arranged below the top portion, the support portion of the support block is arranged on an inner side of the top portion, a top end of the support portion and the top portion form a contact point, and the swing bracket pivotally swings around the contact point on the top end of the support portion.

10. The aroma candle lamp of claim 8, wherein the aroma bottom cover is arranged in the base and has a plurality of through-holes, wherein the aroma fan rotates such that air flows in via the plurality through-holes, passes through the aroma component cavity, and flows out through the aroma fan arranged in the aroma through-hole via a clearance between the flame body and the fixture, so that aroma spreads out from the aroma candle lamp.

11. An aroma candle lamp with a 3D swinging flame, comprising:

a housing comprising a housing body and a base, the housing body and the base surrounding and forming a hollow cavity, the base having a base through-hole, wherein an electronic module and an aroma module are arranged inside the hollow cavity formed by the housing body and the base, and the electronic candle module is arranged above the aroma module;

the electronic candle module comprising a simulating flame comprising a flame body and a light source that is arranged in the flame body, a fixture for fixing the simulating flame, and a swing device for driving the simulating flame to swing, wherein the fixture comprises a left cover and a right cover, the right cover comprising an inside wall with a light source fixing bracket fixed to the inside wall and with the light source installed on the light source fixing bracket, wherein the swing device comprises a swing bracket and a support block having a support portion and a fixing portion connected to one side of the support portion, wherein the fixing portion is directly fixed on an inside wall of the left cover, wherein the swing bracket rests on the support portion, wherein the swing bracket comprises a portion which pivotally swings on a contact point formed with the support block, wherein the flame body is installed on the swing bracket, the swing device further comprising a magnet and a control circuit board with an induction coil arranged to a side of the magnet, the control circuit board configured to generate a signal to cause the induction coil to generate a variable magnetic field to oppose a magnetic field of the magnet and cause the magnet to move and drive the swing bracket to swing, thereby causing the flame body to move; and the aroma module comprising an aroma component housing and an aroma bottom cover which form and surround an aroma component cavity, the aroma bottom cover having a plurality of holes, wherein the aroma bottom cover is arranged in the base through-hole; an aroma component arranged in the aroma component cavity formed by the aroma component housing and the aroma bottom cover; an aroma through-hole formed in the aroma component housing above the aroma component cavity; and an aroma fan arranged in the aroma through-hole, wherein the aroma fan is configured to rotate to drive aroma to spread out from the aroma candle lamp.

12. The aroma candle lamp of claim 11, wherein the aroma component housing is a modular component separate from the housing body and is arranged inside of the hollow cavity in its entirety.

\* \* \* \* \*